United States Patent [19]
Wysor et al.

[11] Patent Number: 6,031,002
[45] Date of Patent: *Feb. 29, 2000

[54] METHOD FOR ENHANCING FEMALE SEXUAL RESPONSE AND A COMPOSITION THEREFOR

[75] Inventors: Michael S. Wysor; Wanda D. Wysor, both of Gray, Tenn.

[73] Assignee: Michael Ebert, New York, N.Y.

[ * ] Notice: This patent is subject to a terminal disclaimer.

[21] Appl. No.: 09/239,887

[22] Filed: Jan. 29, 1999

Related U.S. Application Data

[63] Continuation-in-part of application No. 09/071,436, May 1, 1998, Pat. No. 5,891,915.

[51] Int. Cl.⁷ ..................................................... A61K 31/19
[52] U.S. Cl. ............................................................ 514/573
[58] Field of Search ................................................ 514/573

[56] References Cited

U.S. PATENT DOCUMENTS

| | | | |
|---|---|---|---|
| 4,352,790 | 10/1982 | Johansson et al. | 424/78 |
| 5,773,020 | 6/1998 | Place et al. | 424/426 |
| 5,891,915 | 4/1999 | Wysor et al. | 514/573 |

*Primary Examiner*—Raymond Henley, III
*Attorney, Agent, or Firm*—Michael Ebert

[57] ABSTRACT

A method for enhancing female sexual response in which topically administered to the clitoris of the female subject and the surrounding tissue is a pharmaceutically-acceptable composition whose primary agent is a vasodilator, such as prostaglandin and whose secondary agent is a carrier therefor to deliver it to the clitoris and the surrounding tissue so that it is retained thereby.

17 Claims, No Drawings

METHOD FOR ENHANCING FEMALE SEXUAL RESPONSE AND A COMPOSITION THEREFOR

RELATED APPLICATION

This application is a continuation-in-part of our pending application Ser. No. 09/071,436, filed May 1, 1998, now U.S. Pat. No. 5,891,915 entitled "Method for Enhancing Female Sexual Response and An Ointment Therefor," the entire disclosure of which is incorporated herein by reference.

BACKGROUND OF INVENTION

1. Field of Invention

This invention relates generally to compositions for treating impotence, and more particularly to a method for enhancing female sexuality by topically administering a composition whose primary agent is a vasodilator, such as a prostaglandin, and whose secondary agent is a carrier therefor, which composition is applied to the clitoris and the surrounding tissue of the female subject and is absorbed thereby.

2. Status of Prior Art

The term impotence, as applied to sexuality, usually refers to the inability of a male to attain or sustain penile erection. But it is also applicable to aberrations of sexual function in a female, either because of lack of sexual desire or failure to attain orgasm. Hence female frigidity is effectively, female impotence.

In the treatment of male impotence it is known to use prostaglandins for this purpose. One commercially-available form of this substance is identified as Alprostadil, a naturally occurring prostaglandin E-1. This composition is disclosed in "Mechanisms of Action" in Alprostadil Clinical Pharmacology on "Physicians on Line" (http://www.gsm.com). Also of prior art interest is the Scott U.S. Pat. No. 5,708,031 (1998) which discloses the use of prostaglandin E-2 in the treatment of impotence.

Alprostadil is used to treat impotence in adult males and to maintain the potency of the ductus arteriosus in neonates. Two dosage forms are marketed for treating male impotence: an injection form (Caverjet or Edex) that is directly injected into the corpus cavernosa of the penis, and a trans-urethral product, (Muse), which uses a medicated pellet administered into the urethra.

When treating male impotence, Alprostadil relaxes the smooth muscle of the corpus cavernosum. However, the exact mechanism of this action is unknown. The drug may work by increasing the intracellular concentrations of cyclic AMP. Alprostadil interacts with specific membrane bound receptors, thus stimulating adenylate cyclase and elevating intracellular cyclic AMP, leading to the activation of protein kinase with resultant smooth muscle relaxation. Dilation of the cavernosal arteries is accompanied by increased arterial inflow velocity as well as increased venous outflow resistance. Lacunar spaces expand and blood becomes entrapped secondary to compression of the venule against the tunica albuginea. This process is referred to as the corporal veno-occlusive mechanism.

Alprostadil has heretofore been limited to treating male sexual dysfunction. It has not been used to treat female sexual problems, such as frigidity, nor to enhance female sexual response.

Lack of sexual desire or failure to attain organism is encountered much more frequently in women than in men. It occurs in a significant percentage of neurotic women, as well as in other females who exhibit no signs of psychic disorder. (see: Principles of Neurology—Adams and Victor—Third Edition—McGraw Hill Book Company). Yet heretofore effective pharmaceutical preparations for treating women who have difficulty in responding sexually have not been available.

Of general prior art interest is the 1982 U.S. Pat. No. 4,352,790 of Johansson et al. entitled "Medical Preparation Containing Prostaglandin". This patent discloses a preparation intended for intravaginal or intracervical application. The preparation containing prostaglandin is absorbed in a crosslinked hydroxyl group which is insoluble in water but is capable of swelling in liquids containing water to form a gel.

Also of prior art interest is the 1998 patent to Place et al. entitled "Treatment of Erectile Dysfunction." This patent discloses a vasoactive prostaglandin agent administered to the urethra by means of a penile insert to treat male erectile dysfunction.

SUMMARY OF INVENTION

In view of the foregoing, the main object of this invention is to provide a method for enhancing female sexual response and a composition to be administered topically for carrying out this method.

More particularly, an object of the invention is to provide a method of the above type which topically administers to the clitoris of the female being treated and the surrounding tissue a pharmaceutically-acceptable composition whose primary agent is a vasodilator, such as a prostaglandin of the "E" series, and whose secondary agent is a carrier therefor.

Also an object of the invention is to provide a secondary agent which includes an absorption promoter to enhance the rate of transdermal delivery of the primary agent.

Briefly stated, in a method in accordance with the invention, the non-toxic composition applied topically to exposed surfaces of the clitoris and the surrounding tissue includes a primary agent which is a vasodilator, and a secondary agent that is a carrier for the vasodilator that acts to deliver it to these surfaces so that it is retained thereby.

DESCRIPTION OF INVENTION

We have discovered a method of significantly enhancing female sexual response by treating the clitoris and the surrounding tissues of a female subject with a pharmaceutically acceptable preparations containing a vasodilator, such as prostaglandin of the "E" series, particularly prostaglandin E-1 (Alprostadil). The preferred dosage is that which elicits a maximal sexual response in the subject in a relatively short period, yet has minimal toxicity.

The main beneficiaries of this treatment are:

A. Anorgasmic women (frigid or impotent)

B. Intermittently anorgasmic women

C. Orgasmic women seeking a more pronounced sexual response

This is accomplished by Alprostadil therapy of the clitoris and surrounding tissues by one or more of the following in various permutations and combinations:

1. Decreasing foreplay (the period necessary to prepare women for intercourse).

2. Decreasing the latency period (i.e. the period between orgasms).

3. Decreasing the intercourse time required for orgasm.

4. Multiplying the number of orgasms.

When applied topically to the clitoris and surrounding tissue of a female subject in a pharmaceutically-acceptable formulation in a dosage range sufficient to elicit one or more of the above-mentioned sexual responses (1–4) Alprostadil is then highly effective for this purpose.

An ointment or salve in which the Alprostadil is dispersed is a preferred form of carrier for delivering the composition to the surfaces of the clitoris and surrounding tissues so that it is retained by these surfaces and absorbed thereby. In practice, the ointment may be packaged in a squeeze tube or it may be impregnated in a gauze or foam-plastic sponge applicator.

We have found that the topical administration of no greater than 21.25 micrograms per milliliter of Alprostadil in a pharmaceutically-acceptable ointment base to the clitoris and the tissues immediately surrounding the clitoris is sufficient to produce an absorption of Alprostadil into this region. This acts to dilate the underlying blood vessels to effect enhanced sexual response in three to four minutes (on the average), thereby decreasing the foreplay period for intercourse and the latency period as well as the sexual intercourse time required for orgasm. The treatment also acts to multiply the number of orgasms. But the dosage is not critical, for even a relatively small amount of Alprostadil absorbed in the region of the clitoris will to some degree enhance sexual response.

By a pharmaceutically-acceptable formulation is meant a formulation free of toxicity which satisfies FDA requirements.

Further Formulations:

In a composition in accordance with the invention to be topically applied to the clitoris as well as to surrounding tissues, the primary agent included in the composition is a vasodilator. This acts to dilate the blood vessels underlying the skin to which the composition is applied, thereby stimulating a sexual response.

The vasodilator in the example previously given is a prostaglandin of the "E" series, preferably "E-1". In practice, the vasodilator made a prostaglandin which is an analog of the PGA type or an analog of the PGF.beta.type.

Or the vasodilator may be selected from a group consisting of papaverine, hydralazine, sodium nitroprusside, phenoxybenzamine, phentolamine, prazosin, and vasoactive neuropeptides and their natural and synthetic analogs.

This vasoactive neuropeptide may be selected from a group consisting of vasoactive intestinal peptide (VIP) and peptide N-terminal histidine C-terminal methionelmide and their related natural and synthetic analogs.

The carrier included in the composition for delivering the primary agent to the clitoris and the tissues immediately surrounding the clitoris may take various forms. Thus the carrier, instead of being an ointment base, as previously disclosed, may be take the form of a physiologically-acceptable foam in which the primary agent is dispersed. For the purpose of administering the composition in a foam carrier, use may be made of an air gun injector or a gas-pressurized dispenser to foam the composition onto surfaces of the clitoris and the surrounding tissues. The carrier for the primary agent may also be in a gel which can be dispensed in a manner similar to that of gas-pressurized dispensers for gel-type shaving creams.

Use may also be made of liposome delivery wherein the primary agent is dispersed in a liposome. Liposomes are presently used to convey drugs to target cells or organs, the liposome consisting of an aqueous core enclosed in one or more phospholipid layers.

The applicator for the composition depends on the nature of the carrier. Thus if the carrier for the primary agent in liquid rather than in gel or ointment form, the applicator for this purpose may be a liquid spay gun. But in all instances, the dosage of the primary agent must be such as to elicit a sexual response with minimal toxicity in a relatively short time.

To enhance the rate of transdermal delivery of the primary agent, the carrier therefor may include an absorption promoter, such as dimethylsulfoxide (DMSO) or its analogs.

Or the absorption promoter may be a compound selected from a group consisting of monoalkyl phosphates and pharmaceutically acceptable salts thereof, either alone or in combination with other absorption promoters, such as polyhydroxyesters, long chain fatty acids, polyhydroxyl alcohols and terpenes.

The carrier for the primary agent may include a substantially water-insoluble transdermal penetration enhancing compound selected from the group consisting of C7 to C16 aliphatic group substituted acetals, hemi-acetals and morpholines and further comprising a physiologically acceptable water soluble polar compound selected from the group consisting of alcohols, glycols, lactams, urea, cycloethylene urea, 1,3-dioxolone, 2-methyl-1-3-dioxolone, 1,3-dioxane, 2methyl-1,3-dioxane, morpholine, N-methylmorpholine, N-dimethylformamide, dimethylsulfoxide, methylacetate, ethyllactate, monosaccharides, polysaccharides, amino acids, amino alcohols, diethylamine and cycloethylene carbonate.

The polar compound may be selected from a group consisting of alcohol, glycol, dioxolane, formamide, carbonate, glucose, urea and mixtures thereof. Alternatively, the polar compound may be an alcohol glycol mixture or lactim.

While there has been disclosed preferred formulations for a composition in accordance with the invention and a method of administering this composition so as to enhance female sexual response, it will be appreciated that many changes may be made therein without departing from the spirit of the invention.

We claim:

1. A method for enhancing sexuality in a female having a clitoris comprising the step of topically administering to a surface of the clitoris a composition whose primary agent is a vasodilator and whose secondary agent is a carrier in which the vasodilator is dispersed to deliver it directly to said surface so that it is retained and absorbed thereby, said composition being in a formulation and in a dosage which is substantially free of toxicity and therefore does not give rise to an adverse reaction.

2. A method as set forth in claim 1 in which the secondary agent takes the form of an ointment.

3. A method as set forth in claim 1, in which the secondary agent is in the form of a gel.

4. A method as set forth in claim 1, in which the secondary agent is a foam or spray.

5. A method as set forth in claim 1, in which the vasodilator is dispersed in a liposome.

6. A method as set forth in claim 1, in which the vasodilator is a prostaglandin of the E series.

7. A method as set forth in claim 6, in which the prostaglandin is E-1.

8. A method as set forth in claim 1, in which the vasodilator is selected from a group consisting of papaverine, hydralazine, sodium nitroprusside, phenoxybenzamine, phentolamine, prazosin, and vasoactive neuropeptide and their natural and synthetic analogs.

9. A method as set forth in claim 8, in which the vasoactive neuropeptide is selected from a group consisting of vasoactive intestinal peptide (VIP) and peptide N-terminal histidine C-terminal methionelmide and their related natural and synthetic analogs.

10. A method as set forth in claim 1, in which the composition is also applied topically to tissue surrounding the clitoris.

11. A method as set forth in claim 1, in which the composition is applied to the clitoris by means of a dispenser adapted to eject the composition.

12. A method as set forth in claim 11, in which the dispenser is gas pressurized to eject the composition when the dispenser is actuated.

13. A method as set forth in claim 1, in which the secondary agent includes an absorption promoter to enhance the rate of transdermal delivery.

14. A method as set forth in claim 13, in which the absorption promoter is dimethylsulfoxide and its analogs.

15. A method as set forth in claim 1, in which the vasodilator is a prostaglandin which is an analog of the PGA type or an analog of the PGF.beta.type.

16. A method as set forth in claim 1, in which the composition is delivered manually to said surface by at least one human digit to enable the delivery thereto of a predetermined dosage of the composition.

17. A method as set forth in claim 1, in which the composition is delivered to said surface by means of an applicator adapted to deliver a predetermined dosage of the composition thereto.

* * * * *